United States Patent [19]

Albright et al.

[11] 3,985,820

[45] Oct. 12, 1976

[54] CRACKING PROCESS

[75] Inventors: Charles W. Albright; George E. Keller, II, both of South Charleston, W. Va.

[73] Assignee: Union Carbide Corporation, New York, N.Y.

[22] Filed: Aug. 20, 1974

[21] Appl. No.: 498,990

Related U.S. Application Data

[63] Continuation-in-part of Ser. Nos. 359,675, May 14, 1973, abandoned, and Ser. No. 359,676, May 14, 1973, Pat. No. 3,849,075, which is a continuation-in-part of Ser. No. 252,511, May 8, 1972, abandoned, and Ser. No. 252,512, May 8, 1972, abandoned.

[52] U.S. Cl. .............................. 260/683 R; 201/2.5; 201/25; 208/128; 208/130; 260/669 R
[51] Int. Cl.² .......................................... C07C 3/28
[58] Field of Search ...... 260/683 R, 669 R, 683 PD; 208/128, 130; 201/2.5, 25

[56] References Cited
UNITED STATES PATENTS

| | | | |
|---|---|---|---|
| 2,461,004 | 2/1949 | Soday | 260/683 |
| 2,790,838 | 4/1957 | Schrader | 260/683 |
| 3,494,958 | 2/1970 | Mannsfeld et al. | 260/669 |
| 3,498,753 | 3/1970 | Hokari et al. | 260/683 |
| 3,829,558 | 8/1974 | Banks et al. | 260/683 |

OTHER PUBLICATIONS

Straus et al., Journal of Research of the National Bureau of Standards, vol. 66A, No. 5, Sept.–Oct., 1962, p. 406 relied on.

*Primary Examiner*—Delbert E. Gantz
*Assistant Examiner*—C. E. Spresser
*Attorney, Agent, or Firm*—Marylin Klosty

[57] ABSTRACT

A process for cracking thermoplastic polymers to valuable products, primarily their monomers, comprising the following steps:

a. converting the polymer into a liquid or fluidized stage;

b. introducing the polymer from step (a) in droplet or particulate form into a reaction zone and admixing said polymer with a hot inert gas or mixture of hot inert gases in the reaction zone wherein the weight ratio of gas to polymer is about 1 to about 8 parts of gas per part of polymer; the temperature of the gas is such as to heat the polymer to a temperature in the range of about 800°C. to about 1050°C.; and the residence time in the reaction zone is about 10 to about 100 milliseconds; and c. quenching the recovering product.

20 Claims, No Drawings

1. A process for cracking polyethylene or polypropylene to monomer comprising the following steps:
   a. converting the polymer into a fluidized particulate state;
   b. introducing to a reaction zone a cracking gas comprising steam and the polymer from step (a) and admixing said polymer with the cracking gas in said reaction zone
   wherein the weight ratio of cracking gas to polymer is about 1 to about 8 parts of gas per part of polymer, the temperature of the cracking gas is such as to heat the polymer to a temperature in the range of about 800° C. to about 1050° C., and the residence time of the polymer and the products derived from the cracking thereof in the reaction zone is about 10 to about 100 milliseconds; and
   c. quenching effluent from the reaction zone and recovering the monomer.

2. The process defined in claim 1 wherein the weight ratio of cracking gas to polymer is about 1 to about 3 parts of gas per part of polymer.

3. The process defined in claim 2 wherein the temperature of the cracking gas is such as to heat the polymer to a temperature in the range of about 850° C. to about 1000° C.

4. The process defined in claim 3 wherein said residence time is about 20 to about 60 milliseconds.

5. The process defined in claim 1 wherein the particles of the fluidized polymer are less than about 300 microns in diameter.

6. The process defined in claim 1 wherein the cracking gas is steam.

7. The process defined in claim 1 wherein the cracking gas is a mixture of gases derived from the combustion of hydrogen and oxygen and the steam is mixed together therewith.

8. The process defined in claim 1 wherein the polymer is polyethylene.

9. A process for cracking polyethylene or polypropylene to monomer comprising the following steps:
   a. converting the polymer into liquid droplet form;
   b. introducing to a reaction zone a cracking gas comprising steam and the polymer from step (a) and admixng said polymer with the cracking gas in said reaction zone
   wherein the weight ratio of cracking gas to polymer is about 1 to about 8 parts of gas per part of polymer, the temperature of the cracking gas is such as to heat the polymer to a temperature in the range of about 800° C. to about 1050° C., and the residence time of the polymer and the products derived from the cracking thereof in the reaction zone is about 10 to about 100 milliseconds; and
   c. quenching effluent from the reaction zone and recovering the monomer.

10. The process defined in claim 9 wherein the weight ratio of cracking gas to polymer is about 1 to about 3 parts of gas per part of polymer.

11. The process defined in claim 10 wherein the temperature of the cracking gas is such as to heat the polymer to a temperature in the range of about 850° C. to about 1000° C.

12. The process defined in claim 11 wherein said residence time is about 20 to about 60 milliseconds.

13. The process defined in claim 9 wherein the cracking gas is steam.

14. The process defined in claim 9 wherein the cracking gas is a mixture of gases derived from the combustion of hydrogen and oxygen and the steam is mixed together therewith.

15. The process defined in claim 9 wherein the polymer is polyethylene.

16. A process for cracking polyethylene to ethylene monomer which comprises the following steps:
   a. converting polyethylene into a fluidized particulate state;
   b. introducing into a reaction zone a cracking gas comprising a mixture of combustion gases produced from the essentially complete combustion of a fuel gas and oxygen mixed together with steam, at an inlet temperature of about 950° to about 2000° C.;
   c. introducing the polyethylene from step (a) into the reaction zone and admixing the polyethylene with the cracking gas therein
   wherein the weight ratio of cracking gas to polyethylene is about 1 to about 8 parts of gas per part of polyethylene, the outlet temperature of the reaction zone is in the range of about 800° C. to about 1050° C., the pressure in the reaction zone is in the range of about 5 psig to about 30 psig, and the residence time in the reaction zone of the polyethylene and the products derived from the cracking thereof is about 10 to about 100 milliseconds; and
   d. quenching the effluent from the reaction zone and recovering product comprising ethylene monomer.

17. The process defined in claim 16 wherein the fluidized polyethylene from step (a) is introduced into the reaction zone in a downstream direction.

18. The process defined in claim 16 wherein the outlet temperature of the reaction zone is in the range of about 850° C. and about 1000° C., the pressure in the reaction zone is in the range of about 10 psig to about 25 psig, and the residence time in the reaction zone of the polyethylene and the products derived from the cracking thereof is about 20 to about 60 milliseconds.

19. The process defined in claim 18 wherein the weight ratio of cracking gas to polyethylene is about 1 to about 3 parts of gas per part of polyethylene.

20. The process defined in claim 16 wherein the particles of the fluidized polymer are less than about 300 microns in diameter.

* * * * *

4. The ratio of the volume of tube (A) to the volume of tube (B) can be in the range of about 0.01:1 to about 2.5:1.

Volume of tube (A) or tube (B) is defined by the following equation:

$$\text{Volume} = \frac{(\pi)(\text{diameter or equivalent diameter})^2 (\text{length})}{2}$$

The actual dimensions of the reactor vary according to the use to which the reactor is to be put, e.g., laboratory, pilot plant, or commercial use and, even more so, according to the amount of throughput desired. The number of inlet feed chambers, the number of tube portions, i.e., one or two, and the number of reactors along with many ancillary factors such as the particular economics of the situation must all be considered. An illustration of the range of dimensions, which would be desirable for a feedstock throughput of 50 to 100 pounds per hour, using one inlet feed chamber and one tube portion, is as follows:

| Dimension | Value in Inches |
|---|---|
| a | 12 to 16 |
| b | 0.4 to 1 |
| c | 1 to 2 |
| d | 30 to 70 |
| of orifice | 0.5 to 2 |

Recovery of the effluent mixture of gases and the separation of products therefrom is in all cases accomplished by conventional techniques.

The following example illustrates the invention. Parts and percentages are by weight unless otherwise designated.

EXAMPLE

The system and disc and tube reactor heretofore described are used in this example. More specifically, the procedure followed and the conditions used are as follows:

Initially, a steam generating system is started first by increasing natural gas flow to a furnace and turning on a water pump. A high steam generation rate is used on startup to rapidly heat up the associated piping. The water rate is then adjusted to that required to meet the test conditions. Approximately 1 hour is required for the steam generation conditions to stabilize after adjustment because of the large volume of the steam generating coils. When the steam generation system is at the desired conditions, steam is turned into the mixing section to preheat the reaction system.

When the burner and reactor are at or above the saturation steam temperarture the burner is readied for ignition. Hydrogen is used as fuel for the burner. The burner and reactor are first purged with nitrogen to be sure no combustibles are present. The burner is then ignited. Hydrogen and oxygen flows to the burner are controlled in the proportion for proper combustion, both streams being increased simultaneously to raise the reactor temperature. The function of the burner is to provide a heat source to supply the required sensible heat and heat of reaction.

Polyethylene feedstock is fluidized in a vented vessel by mixing granulated polyethylene scrap with a small amount of nitrogen to act as carrier, about 0.5 percent by weight based on the weight of the polyethylene. The size of the polyethylene granules used is about 100 microns in diameter.

When the reactor is heated almost to operating temperature, flow from the fluidized feeder is initiated. The fluidized polyethylene feed is admitted near the outlet of the mixing section where it is mixed with the steam and the mixture passes into what is designated as the inlet feed chamber. This inlet feed chamber is attached so that its theoretical axis is tangential to the interior surface of the disc wall. Reactor temperature, feed rate, water rate, and combustion rate are controlled to provide tangential flow of the feed/steam mixture and to give the desired residence time.

The reactor effluent is quenched with water to condense residual oils and a major proportion of the steam (about 80 percent by weight). Quench water rate is controlled to maintain the temperature of the stream leaving the quenched zone at 70° C.

The gaseous product leaving the quench zone or separator is cooled to ambient temperature in a condenser. Condensed hydrocarbons and water are collected and the make gas is flared.

Analysis of the products is by gas chromotograph and Mass Spectrometer gas analysis.

The outer dimensions of the reactor used in this example are as follows:

The disc portion, i.e., tube (A), has a length of 0.5 inch and a diameter of 14 inches for a length to diameter ratio of 0.5:14 or 0.036:1.

The tube portion, i.e., tube (B) is a helical coil of cylindrical cross-section having a length of 54 inches and a diameter of 1.5 inches for a length to diameter ratio of 54:1.5 or 36:1.

The volume of tube (A) is $(\pi) (7)^2 (0.5)$ or 77 cubic inches.

The volume of tube (B) is $(\pi) (0.75)^2 (54)$ or 95 cubic inches.

The ratio of the volume of tube (A) to the volume of tube (B) is, therefore, 77:95 or 0.81:1.

The total volume of tubes (A) and (B) is 172 cubic inches or 2820 cubic centimeters.

The ratio of the diameter of the orifice of tube (A) to the diameter of tube (B), both of which are circular cross-sections, is 1:1.
Operating conditions:
Reactor outlet temperature: 950° C. in disc portion and 900° C. at outlet of tube portion.
Cracking gas/polyethylene ratio (by weight): 3 parts of gas per one part of polyethylene
Residence time (milliseconds): 50
Rate of feed: 50 pounds per hour (to reactor)
Rate of gas feed: 150 pounds per hour (to reactor)
Reactor pressure: 15 pounds per square inch gauge
Results:

|  | Yield in percent by weight |
|---|---|
| ethylene | 50 |
| propylene | 12 |
| butadiene | 4 |
| benzene | 6 |
| toluene + xylenes | 6 |
| other | 22 |

We claim:

The mixture of hot gases and polymer enters the inlet feed chamber and then passes into the interior of the disc portion of the reactor.

The inlet feed chamber (or inlet tube) is disposed in the interior near the interior surface of the wall, which describes a hollow cylindrical tube.

There can be one or more inlets depending on the size of the reactor and the feed input per unit time desired, all placed in a similar manner to the feed chamber, preferably at points equally spaced on either side from one another along the wall. Thus two inlets can be connected through the wall at points along its circumference representing 180° and 360°, respectively; three inlets at points along the wall representing 120°, 240°, and 360°, respectively; and four inlets along the circumference at 90°, 190°, 270°, and 360°, respectively.

The disposition of the feed chamber, and similar tubes, near the interior surface of the wall is preferably essentially tangential; however, such disposition is best defined by stating that it be disposed in such a manner that gas flowing from the chamber can flow substantially tangentially to the interior surface of the wall creating a vortex-like flow in the disc portion of the reactor. The size and shape of the chamber, the rate of flow of the feedstock/hot gas mixture, and the direction of flow will have to be considered by the technician in achieving tangential and vortex-like flow in the disc. In practice, the inlet chamber is a tube with openings at both ends placed in a fixed position in the disc so that its theoretical axis is tangential to the inner surface of the wall, and the rate of flow is controlled to achieve the tangential and vortex-like flow.

Although the inlet feed chamber is preferably disposed through the wall, it can be disposed through the top side or bottom side and still achieve a modicum of tangential flow together with vortex-like flow. Although such a disposition is contemplated, it is not the preferred way of carrying out the invention in view of the irregularities of the flow.

The circular wall (or hollow cylindrical tube) has a closure on each end which can be called the top side and the bottom side. The top side is a flat circular surface with no openings, attached to and bounded by the wall.

The bottom side is also a flat circular surface attached to and bounded by the wall having disposed substantially centrally therein an orifice.

The mixture, which now comprises partially cracked polymer, its cracked derivatives, and steam, and/or other cracking gas, passes from the disc portion of the reactor through the orifice into the interior of the hollow tube portion of the reactor. A wall describes the hollow tube of the tube portion which is open at both ends. The tube is in open communication with the disc through the orifice. The wall can be connected to the bottom end or side at the boundaries of the orifice or, if the diameter of the tube is greater than the orifice, the wall of the tube can be connected at other points on the bottom end. In any case, the center of the tube is substantially aligned with the center of the orifice.

The cross-section of the hollow tube can be a variety of shapes although a cylindrical cross-section is preferred. It can, for example, be square, rectangular, triangular, pentagonal, hexagonal, or elliptical, although a mixture of these cross-sections in the same tube is not recommended. The tube can also be a helical coil, which is of value if the space available will not accommodate a straight tube. The end of the tube opposite to the tube's connection to the disc at the orifice is an outlet through which the reactor is in open communication with the downstream portion of the system and, after cracking is essentially completed in the tube portion, the effluent proceeds through this outlet.

Certain ratios concerning dimensions and volumes are critical to the disc and tube reactor. For the purpose of setting out these ratios, the disc portion of the reactor will be referred to as tube (A) and the tube portion of the reactor as tube (B). The important dimensions are as follows:

$a =$ the diameter of tube (A), the disc portion of the reactor. This dimension can also be referred to as the diameter of the cylindrical tube bounded by the disc wall.

$b =$ the length of tube (A). This dimension can also be referred to as the height of the wall.

$c =$ the equivalent diameter of tube (B), the tube portion of the reactor. This dimension can also be referred to as the diameter of the cylindrical tube bounded by the tube wall.

$d =$ the length of tube (B). This dimension can also be referred to as the height of the tube wall.

The dimension of the orifice can be the same as or different than dimension c and will be referred to hereinafter as the equivalent diameter of the orifice of tube (A).

It should be noted that dimensions $a$, $b$, and $c$ are outer dimensions which include the thickness of the reactor walls. This was an arbitrary selection, i.e., interior dimensions could have just as well been used.

Equivalent diameter is used to describe dimension $c$ and the dimension of the orifice simply because the tube and orifice do not have to be cylindrical cross-sections, but can take on a variety of shapes. Various kinds of shapes were mentioned heretofore for the tube and this is applicable to the orifice also. Equivalent diameter is a convenient way of defining both non-cylindrical cross-sections and cylindrical cross-sections with one term. The mathematical abbreviation for equivalent diameter is $D_{eq}$ and the equation defining this term is as follows:

$$D_{eq} = \frac{4 \times \text{cross-sectional area}}{\text{perimeter of cross-sectional area}}$$

Where the cross-sectional area of the tube varies along its length an average equivalent diameter can be used, but tubes of varying cross-section are considered impractical and are not recommended. The shape of the orifice can be different from that of the tube, however, without creating any impracticalities.

The critical ratios are as follows:

1. Tube (A) can have a length ($b$) to diameter ($a$) ratio in the range of about 0.1:1 to about 1:1 and such ratio is preferably in the range of about 0.03:1 to about 1:1.

2. The ratio of the equivalent diameter of the orifice of tube (A) to the equivalent diameter ($c$) of tube (B) can be in the range of about 1:1 to about 0.1:1 and is preferably in the range of about 1:1 to about 0.25:1.

3. Tube (B) can have a length ($d$) to equivalent diameter ($c$) ratio in the range of about 5:1 to about 200:1 and such ratio is preferably in the range of about 10:1 to about 100:1.

order of increasing particle size, as follows: two-fluid nozzles, hydraulic hollow cone nozzles, and hydraulic flat spray nozzles.

The polymer is injected into the mixture of combustion gases at a ratio of about 1 to about 8 parts by weight of cracking gas per part by weight of polymer, and, preferably, in a ratio of about 1 to about 3 parts of cracking gas per part of polymer and under a total inlet pressure sufficient to operate the injection device, which can be about 100 psig to about 1000 psig and or about 500 psig to about 800 psig.

The temperature of the cracking gas is most easily maintained by introducing the polymer as close to the upstream end of the reactor as practicable so that, along with the insulating qualities of the materials used to construct the reactor, very little heat loss occurs in transit.

Simultaneous control of the inlet temperature of the polymer by using a jacketed inlet with a coolant passing therethrough to prevent overheating and subsequent coking of the inlet.

The temperature of the cracking gas in the region of injection (it should be remembered that the cracking gas may include the products of the combustion of oxygen with the fuel gas plus the steam, in partially dissociated form) is generally determined from heat balance calculations or from flow-pressure measurements across the constricted throat section. Inlet steam temperatures and temperatures in the downstream portion of the reactor are measured with thermocouples.

The outlet temperature of the reaction zone (as noted, this is considered the temperature to which the polymer is heated) is maintained in the range of about 800° C. to about 1050° C., and, preferably, in the range of about 850° C. to about 1000° C.; the pressure of the reaction zone is maintained in the range of about 5 psig to about 30 psig and, preferably, about 10 psig to about 25 psig; and the residence time of the polymer and products thereof in the reaction zone is kept within about 10 milliseconds to about 100 milliseconds and, preferably, about 20 to 60 milliseconds.

Heat loss control has been mentioned previously. One of the ways heat loss is controlled is through the materials used in constructing the apparatus, particularly the reaction section. Alumina, mullite, zerconia, graphite, silicon carbide, and magnesia can be used with alumina or mullite being preferred as liners for a stainless steel reactor. The burner and reactor inlet portion are liquid cooled, in any case, to avoid excessive temperatures. Stainless steel fittings can be used such as those made of AISI types 310, 321, 330, and 333. Loss of heat contributes to poor economics due to poor thermal efficiency.

Many types of reactors can be used, e.g., those described in United States patent applications Ser. Nos. 359,675 and 359,676. As noted above, a simple hollow cylindrical tube reactor having a length to diameter ratio of about 5:1 to about 200:1 can also be used.

The effluent from the reaction zone is then passed into the quenching zone. The temperature in the quenching zone must be sufficiently low to stop the reaction essentially instantaneously. Conventional quenching techniques can be used such as a heavy oil quench or a light oil quench with a heavy oil wall flush to avoid fouling. A water quench can also be used. Usually quench nozzles are used in conventional systems and the axes of the nozzles are preferably perpendicular to the flow of the effluent, i.e., the quench spray or stream is directed perpendicular to the flow. The pressure drop across the quench zone is usually less than about one psi. Heat exchangers may be used in the quench zone as well as spray nozzles or other conventional quench means.

Pre-quenching may be used to bring the temperature down to the lower limit in the reaction zone, i.e., about 750° C. outlet temperature.

The effluent then passes from the quenching zone and is recovered and separated by various conventional means. Where the polymer is polyethylene, a typical effluent contains ethylene, ethane, propadiene, propylene, acetylene, butadiene, benzene, and other products and also includes small amounts of methane and hydrogen as well as oxidation products such as carbon dioxide, carbon monoxide, and water with a yield of ethylene of about fifty percent by weight.

The reactors referred to in applications Ser. Nos. 359,675 and 359,676 are typical of those with which this process can be used.

One of those reactors is defined as comprising

A. a hollow cylindrical tube having (i) a first end closure and a second end closure, at least one of said end closures being provided with an orifice disposed substantially centrally therein; and (ii) at least one hollow inlet feed chamber open at both ends passing through the cylindrical surface described by tube (A), one end of said feed chamber being disposed in the interior of the tube at about its periphery in such a manner that vapor, which is passed through said chamber, will flow substantially tangentially to the inner surface described by cylindrical tube (A), provided the rate of flow is sufficient therefor, creating a vortex-like flow within tube (A); and B. at least one hollow tube open at both ends; wherein;
  a. one end of tube (B) is connected to tube (A) at its orifice in substantially concentric alignment therewith and in open communication with tube (A);
  b. tube (A) has a length to diameter ratio of about 0.01:1 to about 1:1;
  c. the ratio of the equivalent diameter of the orifice of tube (A) to the equivalent diameter of tube (B) is about 1:1 to about 0.1:1.
  d. tube (B) has a length to equivalent diameter ratio of about 5:1 to about 200:1; and
  e. the ratio of the volume of tube (A) to the volume of tube (B) is about 0.01 to about 5:1.

The reactor can be made from various materials, in addition to those mentioned above, the preferred material being stainless steel, e.g., AISI type 316 stainless steel. Other representative materials from which the reactor can be made are AISI types 304 and 347 stainless steel; an alloy containing approximately 76% nickel, 16% chrome, and 6% iron; as well as various ceramics with high-temperature stability.

The thickness of the reactor walls can be decided upon conventional lines and is not critical to the invention. Temperatures, pressures, longevity, economics, and available materials should be considered when making the decision.

The preferred embodiment of the reactor described here can be called a disc and tube reactor and subsequent references made in the description may refer to the disc portion of the reaction or the tube portion of the reactor.

total oxygen inlet pressure is about 25 psig (pounds per square inch gauge) to about 500 psig and is preferably about 100 psig to about 200 psig.

The fuel gas is also introduced through one or more inlet lines at or near the upstream end of the burner zone.

The fuel gas is made up of hydrogen and from 0 to about 90 parts by weight of another fuel gas per part by weight of hydrogen. The other fuel gases are preferably methane or propane, but can be any gaseous or liquid fuel.

It is preferred to use either hydrogen alone or a ratio of about 1 to about 50 parts by weight of other fuel gas per part by weight of hydrogen. The total inlet pressure of the hydrogen and other fuel gas is about 75 psig to about 800 psig, and preferably about 150 psig to about 400 psig.

At one of the points of entry for the oxygen or the fuel gas or at both or all, steam is introduced into the burner. The steam enters the burner at a total inlet pressure of about 25 psig to about 800 psig and preferably about 100 psig to about 400 psig. The ratio of oxygen to steam is about 0.1 part by weight to about 50 parts by weight of oxygen per part by weight of steam preferably about 0.5 part by weight to about 10 parts by weight of steam.

As noted, steam can be introduced at both the oxygen inlet and the hydrogen inlet to assist in the intense mixing in the burner and promote homogeneity. If the oxygen is not mixed properly and essentially complete combustion is not attained, the oxygen gets into the reactor zone and destroys the polymer/monomer by forming the usual carbon oxide compounds. Advantages of steam mixing in the burner zone, in addition to more complete combustion, are the lowering of temperatures and associated heat losses in the burner zone and the lowering of the overall heat losses as a result of the avoidance of secondary steam-mixing chambers. Steam can be introduced directly into the reaction zone, however, provided the correct temperature is achieved thus eliminating the burner as such.

The steam, prior to its introduction into the burner or reactor, is superheated to a temperature of about 200° C. to about 1200° C. and preferably about 700° C. to about 1100° C. by conventional methods. Where a burner is used, the steam temperatures in the lower part of the range are satisfactory, but where there is no burner, steam temperatures which will heat the polymer to about 800° C. to about 1050° C. are necessary. It should be understood, as a practical matter, that the temperature to which the polymer is heated, i.e., in the range of about 800° C. to about 1050° C., is measured at the outlet of the cracking reactor, i.e., it is the outlet temperature of the reactor. This generally means that the superheated steam must be in the range of about 950° C. to about 2000° C. to achieve the cracking temperatures.

The ratio of fuel gas to oxygen is about stoichiometric and preferably is a slightly fuel rich mixture.

The pressure inside the burner zone is about 25 psig to about 500 psig and preferably about 100 psig to about 200 psig; and the outlet temperature is about 950° C. to about 2000° C. and preferably about 1400° C. to about 1800° C.

A fuel-oxygen mixture is ignited at a point in the burner zone usually near the inlet with an igniter. Essentially complete combustion is determined by conventional analytical techniques and adjustments are made to the process conditions to attain this goal.

Instead of a burner system, a regenerative furnace can be used.

The mixture of combustion gases with or without steam, or steam where used by itself, or any hot gas or mixture of hot gases used for cracking in the reactor will be referred to hereinafter as the "cracking gas".

The cracking gas passes from the burner into the reaction zone. The passage can take place through a constricted throat section having a diameter, which will maintain a suitable pressure in the burner and length, which will avoid unnecessary heat losses. When using the constricted throat section, the cracking gas then enters the much wider reaction zone where the gas expands. Although the gas enters the reaction zone at the outlet velocity derived from the constricted throat section which may be sonic velocity, the velocity is slowed by the expansion to that of about 50 feet per second to about 500 feet per second and preferably about 100 feet per second to about 250 feet per second.

The fluidized polymer is then introduced just before the constricted zone section or just after it. If there is no constricted zone, the polymer can be introduced at the downstream end of the burner or the upstream end of the reactor. Since cracking begins immediately on entry of the polymer, the reaction zone can be said to begin at the point of its entry even though this may take place in the burner, the passage between burner and reactor, or reactor. If liquid polymer is used, it is preferably atomized, the idea being to have droplets or, in the case of fluidized polymer, small particles in the reactor, which will be contacted by the cracking gas, heated rapidly, and cracked more efficiently simply because of the higher exposed surface area.

The reactor can be a hollow cylindrical tube having a length to diameter ratio of about 5:1 to about 50:1 and preferably about 7:1 to about 20:1, or as described in the aforementioned patent applications. In all of the reactions, it is preferable to make the injection of polymer close to the upstream end of the reactor and, in any case, in the tubular reaction not more than halfway along the reaction zone for the sake of thermal efficiency.

Prior to the introduction of the polymer into the reaction zone, the polymer is preferably preheated to temperatures in the range of about 50° C. to about 400° C. and, preferably, about 250° C to about 350° C. The preheating step is preparatory to handling the polymer in the reactor, which can be controlled in terms of viscosity and temperature so that the polymer does not become too viscous prior to injection and, on the other hand, so that it does not atomize or vaporize prior to injection.

The polymer is preferably introduced into the reaction zone in a downstream direction, but can be introduced in other directions if desired.

Various types of nozzles can be used for the introduction of polymer into the reaction zone. The nozzles are generally made of stainless steel, e.g., AISI type 321 or AISI type 310, and may be cooled with various types of coolants such as water or steam by passing the coolant through a jacket surrounding the inlet portion. Nozzles less than 10 GPM (GPM = U.S. gallons per minute) in size are suggested. The nozzles can be inserted into the reactor at various angles, which may be helpful in temperature control. Suitable nozzles can be classified, in

CRACKING PROCESS

This application is a continuation-in-part of applications Ser. Nos. 359,675, now abandoned and 359,676, now U.S. Pat. No. 3,849,075 both filed on May 14, 1973, which, in turn are continuations-in-part of applications Ser. Nos. 252,511 and 252,512, respectively, both filed on May 8, 1972 both abandoned.

FIELD OF THE INVENTION

This invention relates to the thermal cracking of thermoplastic polymers and, more particularly, to a process for cracking such thermoplastic polymers to obtain high yields of their monomers.

DESCRIPTION OF THE PRIOR ART

Pyrolysis of polymers has been conducted in the laboratory for many years and it is known that most polymers degrade to such an extent that less than about five percent monomer is recovered. Although the monomers of the more important commercial polymer are valuable chemical intermediates and there is a great quantity of polymer scrap available, no one, heretofore, has proposed that the environmental problem posed by this scrap be solved by converting the polymer back to the useful monomer simply because of the low yields obtained on pyrolysis not only of monomer, but of any valuable commercial product.

SUMMARY OF THE INVENTION

An object of this invention, therefore, is to provide a method for converting thermoplastic polymer to monomer and other valuable products in high yields.

Other objects and advantages will become apparent hereinafter.

According to the present invention, a method has been discovered for producing monomer which comprises the following steps:

a. converting thermoplastic polymer into a liquid or fluidized state;

b. introducing the polymer from step (a) in droplet or particulate form into a reaction zone and admixing said polymer with a hot inert gas or mixture of hot inert gases in the reaction zone wherein the weight ratio of gas to polymer is about 1 to about 8 parts of gas per part of polymer; the temperature of the gas is such as to heat the polyethylene to a temperature in the range of about 800° C. to about 1050° C.; and the residence time in the reaction zone is about 10 to about 100 milliseconds; and c. quenching and recovering monomer.

DESCRIPTION OF THE PREFERRED EMBODIMENT

The type of apparatus which can be used and many of the techniques and the terminology appearing in the specification have been disclosed previously. Representative publications are U.S. Pat. Nos. 2,934,410 and 3,408,417, which are incorporated by reference herein. Similar information can be found in applications Ser. Nos. 359,675 and 359,676, also incorporated by reference herein.

The instant process is particularly adapted to the cracking of all thermoplastic polymers, the most notable being polyethylene, polypropylene, polystyrene and styrene copolymers, and polyvinylchloride. It should be understood that the molecular weight of the polymers is irrelevant to subject process, the only proviso being that the thermoplastic polymer can either be melted to a liquid without degradation or comminuted to small particles which can be fluidized. Any form of polymer can be used, the simplest way of proceeding being to take the solid polymer and comminute it into small particles or granules, for example, those having a diameter of less than about 300 microns and, preferably, less than about 100 microns. The smaller the particle the better for the process; however, too small a particle is impractical because of the high cost of producing it. The next step is that of fluidizing the granules by mixing with a small amount of a carrier such as nitrogen, hydrogen, methane, or various other inert gases or fuel gases or mixtures therof. The fluidization usually takes place in a vented vessel adapted particularly for such a technique and the fluidized material is then introduced into the reactor section of the cracking apparatus through a feed line while monitoring the flow rate to provide the correct ratio of cracking gas to polymer. Another way of proceeding is to melt solid polymer at temperatures below degradation temperatures into a liquid, which is introduced into the cracking apparatus in atomized or droplet form.

Apparatus-wise, the system described here is made up of a reactor, preferably adiabatic, and a quenching zone, which can be an integral part of the reactor or independent thereof. There may be, and preferably is, a burner where the hot inert gas is prepared before it is sent to the reactor. The reactor can be a tube shaped structure, or convex lens and tube or disc and tube shaped structures as shown in the above-mentioned patent applications. Inlet nozzles or other inlet means and various fittings round out the picture.

The burner can be of the type described in U.S. Pat. No. 3,074,469. It can be made of various metals and metal alloys, the preferred material being stainless steel, e.g., AISI (American Iron and Steel Institute) type 321 stainless steel. Other representative materials from which the reactor can be made are AISI type 310 stainless steel and copper. Ceramic burners can also be used. Preferred burners have mixing devices and can be operated under conditions to insure the instantaneous and complete mixing of fuel, oxygen and steam. Various means for cooling the burner are available such as passing steam or water through jackets. The construction of the burner is such that the combustion gases can be in a highly turbulent state within the burner. The structure of the internal portion, the rate and direction of flow of the gases entering the burner, the temperature and pressure, all combine to provide essentially complete combustion in order to avoid having uncombusted gases in a reaction zone that detract from the efficiency of the process.

The hot inert gas is one gas or a mixture of gases which will substantially not react with the thermoplastic polymer, its monomer, or any of the products of cracking the polymer. It can be steam, or a fuel gas mixture such as the products of combustion of hydrogen and oxygen, or a mixture of both, which is preferred.

A typical burner, the gaseous mixture used therein, and its function can be described as follows:

Oxygen is introduced through an inlet line at or near the upstream end of a burner zone which is generally a modified cylindrical tube. The dimensions of the burner zone are not critical although the larger the tube or chamber, the more gases it can handle. There can be several oxygen inlets rather than one, if desired. The

UNITED STATES PATENT OFFICE
CERTIFICATE OF CORRECTION

Patent No. 3,985,820  Dated October 12, 1976

Inventor(s) Charles W. Albright and George E. Keller, II

It is certified that error appears in the above-identified patent and that said Letters Patent are hereby corrected as shown below:

In the Abstract, fifth line thereof, for "stage" read -- state --. Column 1, line 21, for "polymer" read -- polymers --. Column 2, line 14, for "therof" read -- thereof --. Column 4, line 43, for "reaction" read -- reactor --. Column 9, line 56, for "temperarture" read -- temperature --.

Signed and Sealed this fifth Day of July 1977

[SEAL]

Attest:

RUTH C. MASON
Attesting Officer

C. MARSHALL DANN
Commissioner of Patents and Trademarks